(12) United States Patent
Sakurada

(10) Patent No.: US 11,483,515 B2
(45) Date of Patent: Oct. 25, 2022

(54) IMAGE RECORDING AND REPRODUCTION APPARATUS, IMAGE RECORDING METHOD, AND ENDOSCOPE SYSTEM

(71) Applicant: OLYMPUS CORPORATION, Tokyo (JP)

(72) Inventor: Yusuke Sakurada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/180,946

(22) Filed: Feb. 22, 2021

(65) Prior Publication Data

US 2021/0203875 A1 Jul. 1, 2021

Related U.S. Application Data

(63) Continuation of application No. PCT/JP2018/031439, filed on Aug. 24, 2018.

(51) Int. Cl.
| | | |
|---|---|---|
| *H04N 5/77* | (2006.01) | |
| *A61B 1/00* | (2006.01) | |
| *G11B 27/10* | (2006.01) | |

(52) U.S. Cl.
CPC ............. *H04N 5/77* (2013.01); *A61B 1/0002* (2013.01); *A61B 1/0004* (2022.02);
(Continued)

(58) Field of Classification Search
None
See application file for complete search history.

(56) References Cited

U.S. PATENT DOCUMENTS

| | | | | |
|---|---|---|---|---|
| 2010/0281375 A1* | 11/2010 | Pendergast | ............. | G11B 27/34 715/723 |
| 2014/0043455 A1* | 2/2014 | Fukuda | ................ | A61B 1/0005 348/74 |

(Continued)

FOREIGN PATENT DOCUMENTS

| | | |
|---|---|---|
| JP | 2001-008168 A | 1/2001 |
| JP | 2005-40223 A | 2/2005 |

(Continued)

OTHER PUBLICATIONS

International Search Report dated Sep. 25, 2018 issued in PCT/JP2018/031439.

*Primary Examiner* — Eileen M Adams
(74) *Attorney, Agent, or Firm* — Scully, Scott, Murphy & Presser, P.C.

(57) ABSTRACT

An image recording and reproduction apparatus includes: a record data generation circuit configured to generate record data based on an inputted video signal; an operation input device configured to receive a signal generated based on an operation of one or more persons, for one or more operation instructors that accept an operation for adding chapter information to the video signal; an operation system determination circuit configured to determine at least one of the operation instructor generating the signal received by the operation input device, and a person performing the operation, and output a determination result; and a first processor configured to cause the record data generation circuit to generate the record data that associates the chapter information with the video signal, by generating chapter information of a chapter type based on the determination result of the operation system determination circuit, and supplying the information to the record data generation circuit.

12 Claims, 10 Drawing Sheets

(52) U.S. Cl.
CPC ........ *A61B 1/0005* (2013.01); *A61B 1/00006* (2013.01); *G11B 27/102* (2013.01)

(56) References Cited

U.S. PATENT DOCUMENTS

2017/0212603 A1\* 7/2017 Rahme .................. G06F 3/0231
2018/0090176 A1 3/2018 Yamada

FOREIGN PATENT DOCUMENTS

| | | |
|---|---|---|
| JP | 2006-122375 A | 5/2006 |
| JP | 2006-271870 A | 10/2006 |
| JP | 2006-271871 A | 10/2006 |
| JP | 2018-50921 A | 4/2018 |
| WO | WO 2012/165381 A1 | 12/2012 |

\* cited by examiner

FIG. 3

| No. | System1,CHAPTER POSITION | System2,CHAPTER POSITION | System3,CHAPTER POSITION |
|---|---|---|---|
| 1 | 00:05:25 | 00:07:40 | 00:14:20 |
| 2 | 00:19:36 | 00:22:12 | 00:27:51 |
| 3 | 00:30:03 | 00:30:15 | 00:44:28 |
| ... | ... | ... | ... |

FIG. 4

```
...
[Sys1ChapterInfo]
Sys01chap001=00:05:25
Sys01chap002=00:19:36
Sys01chap003=00:30:03

[Sys2ChapterInfo]
Sys02chap001=00:07:40
Sys02chap002=00:22:12
Sys02chap003=00:30:15

[Sys3ChapterInfo]
Sys03chap001=00:14:20
Sys03chap002=00:27:51
Sys03chap003=00:44:28

[x x x x]
...
```

```
...
[ChapterInfo]
Sys01chap001=00:05:25
Sys01chap002=00:19:36
Sys01chap003=00:30:03

| No. | System1 | | System2 | | System3 | |
|---|---|---|---|---|---|---|
| | TIME PERIOD INFORMATION | USER | TIME PERIOD INFORMATION | USER | TIME PERIOD INFORMATION | USER |
| 1 | 00:05:25 | A | 00:07:40 | A | 00:14:20 | B |
| 2 | 00:19:36 | B | 00:22:12 | A | 00:27:51 | C |
| 3 | 00:30:03 | C | 00:30:15 | C | 00:44:28 | A |
| ... | ... | | ... | | ... | |

FIG. 9

```
...
[Sys1ChapterInfo]
Sys01_USER_Achap001=00:05:25
Sys01_USER_Bchap002=00:19:36
Sys01_USER_Cchap003=00:30:03

[Sys2ChapterInfo]
Sys02_USER_Achap001=00:07:40
Sys02_USER_Achap002=00:22:12
Sys02_USER_Cchap003=00:30:15

[Sys3ChapterInfo]
Sys03_USER_Bchap001=00:14:20
Sys03_USER_Cchap002=00:27:51
Sys03_USER_Achap003=00:44:28

[x x x x]
...
```

```
...
[ChapterInfo]
Sys01_USER_Achap001=00:05:25
Sys01_USER_Bchap002=00:19:36
Sys01_USER_Cchap003=00:30:03

[xxxx]
...
```

IMAGE RECORDING AND REPRODUCTION APPARATUS, IMAGE RECORDING METHOD, AND ENDOSCOPE SYSTEM

CROSS REFERENCE TO RELATED APPLICATION

This application is a continuation application of PCT/JP2018/031439 filed on Aug. 24, 2018, the entire contents of which are incorporated herein by this reference.

BACKGROUND OF THE INVENTION

1. Field of the Invention

The present invention relates to an image recording and reproduction apparatus that records an image, an image recording method, and an endoscope system.

2. Description of the Related Art

Conventionally, endoscopes have been widely adopted in a medical field and the like. Medical images obtained by endoscopes are recorded in various media for diagnosis and medical case recording. In recent years, as the capacities of recording media have been increasing, recording of movies from endoscopes has tended to be performed.

For example, in procedures and examinations using endoscopes, not only endoscope images, ultrasound images, and X-ray images during the procedures and examinations, but also various images (hereinafter referred to as medical images), such as images around hands of operators, and images of situations in rooms, are sometimes recorded as movies. Among such image recording apparatuses, some apparatuses can achieve a recording operation through a scope switch or the like, which is provided not only at an image recording apparatus main body but also at an endoscope.

For example, International Publication No. 2012-165381 discloses a technology that records a medical images in a first recording area over the entire period of a first period, and records a copy of the medical image in a second recording area in a predetermined second period before and after user operation timing.

For the sake of recording medical cases, it is conceivable that a medical image is used as a backup of an evidence image or the like, and is used as an educational material. For example, as for an important anatomical scene in a medical case, recorded images can be shared in an academic conference or a conference in a hospital to be utilized for education for junior doctors. For a technical certification system, endoscopic procedures and the like can be recorded, and the procedures can be certified from the recorded images.

Recording for a backup requires recording of an entire medical case. For example, in a surgical operation, image recording is performed for a relatively long time period. On the other hand, images used for education are often images in a partial period in a procedure or an examination period. Accordingly, when the recorded images obtained by recording an entire medical case are used for education, efforts are sometimes required to search for a desired scene.

Accordingly, a method is conceivable that records images while adding chapter information for designating a reproduction point by a scope switch or the like, in the middle of medical image recording. Use of the chapter information allows the reproduction point to be cued, and an image of a desired scene can be easily retrieved.

SUMMARY OF THE INVENTION

An image recording and reproduction apparatus according to an aspect of the present invention includes: a record data generation circuit configured to generate record data based on an inputted video signal; an operation input device configured to receive a signal generated based on an operation of one or more persons, for one or more operation instructors that accept an operation for adding chapter information to the video signal recorded in the record data generation circuit; an operation system determination circuit configured to determine at least one of the operation instructor generating the signal received by the operation input device, and a person performing the operation, and output a determination result; and a first processor configured to cause the record data generation circuit to generate the record data that associates the chapter information with the video signal, by generating chapter information of a chapter type based on the determination result of the operation system determination circuit, and supplying the information to the record data generation circuit.

An endoscope system according to an aspect of the present invention includes: the image recording and reproduction apparatus described above; and an endoscope, wherein the endoscope functions as the operation instructor.

An image recording method according to an aspect of the present invention includes: generating record data based on an inputted video signal; receiving, as an operation input signal, a signal generated based on an operation of one or more persons, for one or more operation instructions that accept an operation for adding chapter information to the video signal recorded in the record data; determining at least one of the operation instruction, and a person performing the operation, based on the operation input signal, and outputting a determination result; and generating the record data that associates the chapter information with the video signal, by generating chapter information of a chapter type based on the determination result of the operation system, and supplying the information to the record data.

BRIEF DESCRIPTION OF THE DRAWINGS

FIG. 3 is an explanatory diagram showing an example of a chapter information table;

FIG. 4 is an explanatory diagram showing an example of chapter information metadata;

FIG. 8 is an explanatory diagram for illustrating a second embodiment of the present invention;

FIG. 9 is an explanatory diagram for illustrating the second embodiment of the present invention;

DETAILED DESCRIPTION OF THE PREFERRED EMBODIMENTS

Hereinafter, with reference to the drawings, embodiments of the present invention are described in detail.

First Embodiment

Figure 1:
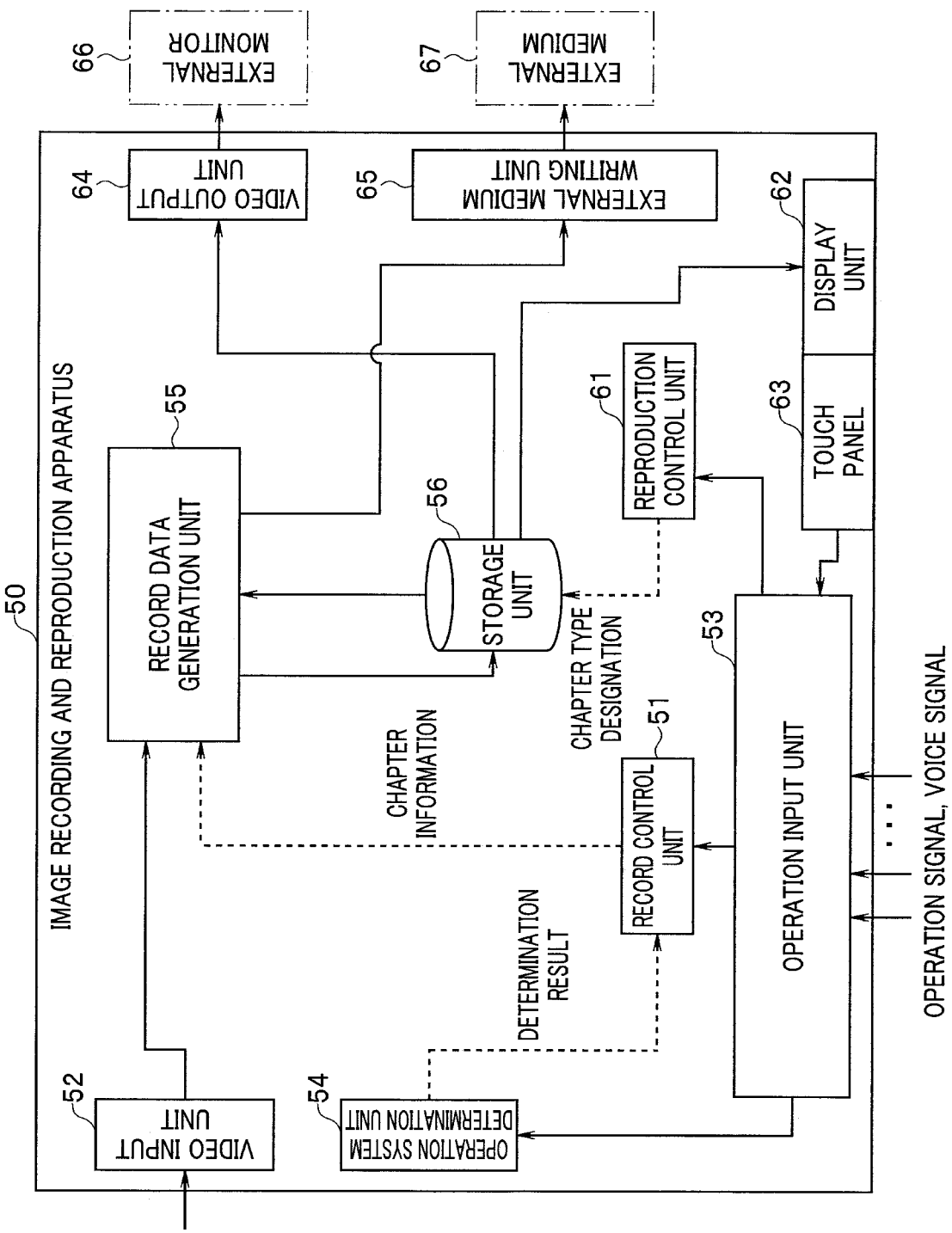
FIG. 1 is a block diagram showing an image recording and reproduction apparatus according to a first embodiment of the present invention.
Figure 2:
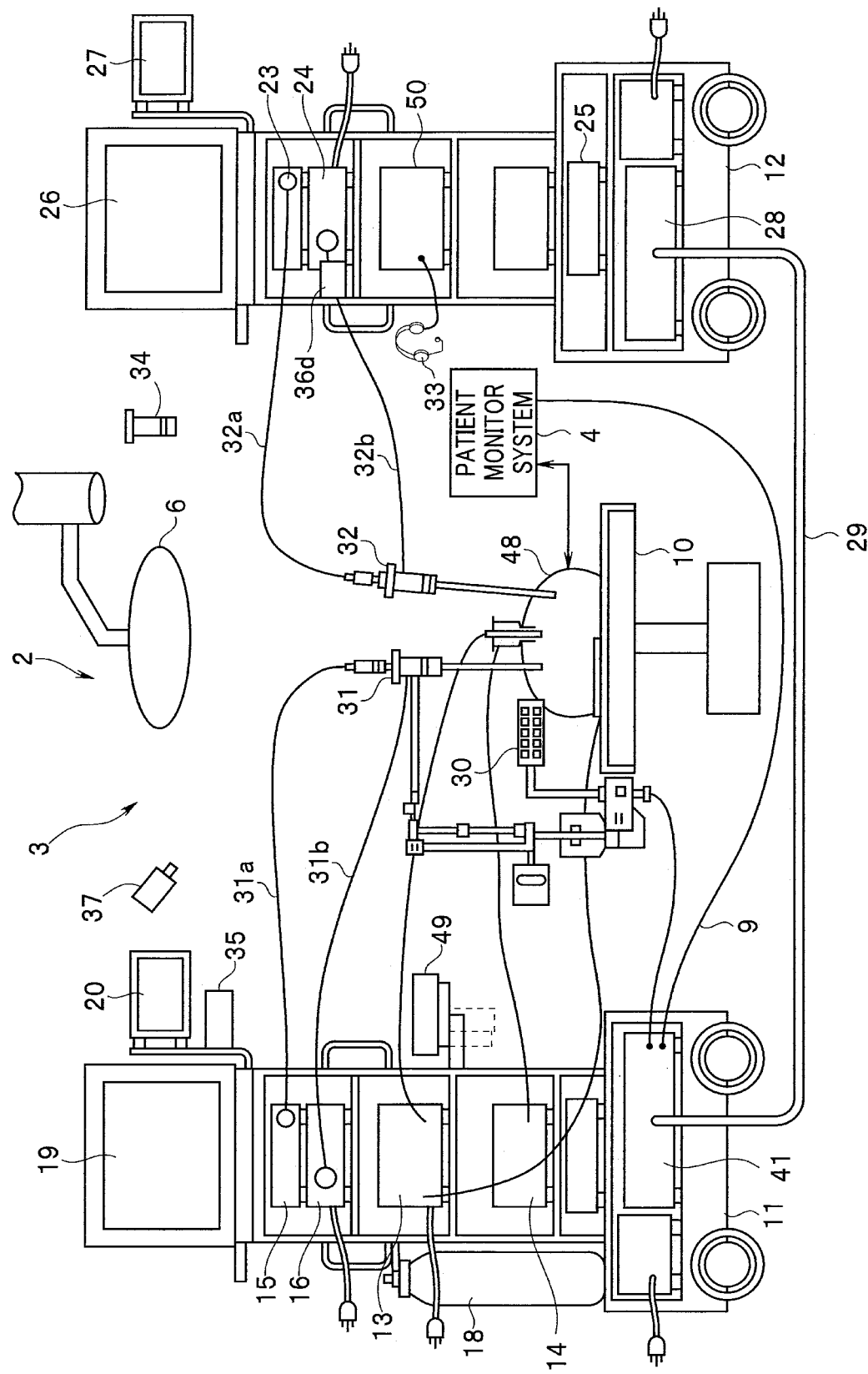
FIG. 2 is an explanatory diagram showing an endoscope system where the image recording and reproduction apparatus in FIG. 1 is arranged.

FIG. 1 is a block diagram showing an image recording and reproduction apparatus according to a first embodiment of the present invention. FIG. 2 is an explanatory diagram showing an endoscope system where the image recording and reproduction apparatus in FIG. 1 is arranged.

The present embodiment classifies the chapter information into multiple types (systems), associates a person or a device with each of chapter types (also referred to as chapter systems), and records the chapter information. For example, by setting devices for which recording of chapter information of predetermined chapter types can be designated, and by associating each device with a person, the chapter information of chapter types different among individual persons (devices) can be recorded.

Typically, in an operating room, multiple doctors and nurses are arranged to allow procedures to be performed, and during procedures, devices that the respective persons operate are often predetermined. In the present embodiment, during medical image recording, in response to an operation of a device by each person, the chapter information of the corresponding chapter type is recorded. Note that in the present embodiment, an example of medical image recording is described, but the types of images to be recorded are not specifically limited, and the technology is applicable not only to the medical devices but also to recording and reproduction apparatuses for various types of images.

First, with reference to FIG. 2, the situations of arrangement of an image recording and reproduction apparatus 50 in an operating room 2 are described. As shown in FIG. 2, an endoscope system 3 arranged in the operating room 2 is provided with a surgical table 10 on which a patient 48 lies, and a system controller 41 that controls medical devices, such as an electric scalpel device 13. In the operating room 2, a first cart 11 and a second cart 12 are provided, and the system controller 41 is mounted on the first cart 11.

The first cart 11 is mounted with medical devices that are equipment to be controlled, including, for example, devices that are the electric scalpel device 13, an insufflation device 14, a video processor 15, and a light source device 16, and a gas cylinder 18 filled with carbon dioxide. The video processor 15 is connected to a first endoscope 31 through a camera cable 31a.

The light source device 16 is connected to the first endoscope 31 through a light guide cable 31b. The first cart 11 is mounted with a display device 19, a first centralized display panel 20, an operation panel 49 and the like. The display device 19 is, for example, a TV monitor, and displays an endoscope image and the like from the video processor 15.

The centralized display panel 20 serves as display means that can selectively display entire data during an operation. The operation panel 49 includes a display screen, such as a liquid crystal display, and a touch sensor or the like provided integrally on the display screen, and serves as a centralized operation device that a nurse or the like residing in an unsterilized area operates.

The surgical table 10, a shadowless lamp 6, the electric scalpel device 13, the insufflation device 14, the video processor 15, and the light source device 16 are connected to the system controller 41, which is a centralized control device, through a communication line, not shown.

The first cart 11 is provided with an RFID (radio frequency identification) terminal 35 that can wirelessly read and write individual ID information on objects, through ID tags embedded in the first endoscope 31, and a treatment instrument, such as the electric scalpel device 13.

On the other hand, the second cart 12 is mounted with a video processor 23, a light source device 24, an image processing device 25, a display device 26, a second centralized display panel 27, and the image recording and reproduction apparatus 50, which are equipment to be controlled. The video processor 23 is connected to a second endoscope 32 through a camera cable 32a. The light source device 24 is connected to the second endoscope 32 through a light guide cable 32b.

The display device 26 displays an endoscope image and the like captured by the video processor 23. The second centralized display panel 27 is configured to be capable of selectively displaying entire data during an operation.

The video processor 23, the light source device 24, the image processing device 25, and the image recording and reproduction apparatus 50 are connected to a relay unit 28 mounted on the second cart 12, via communication lines, not shown. The relay unit 28 is then connected to the system controller 41 mounted on the first cart 11, through a relay cable 29.

The system controller 41 can thus control the video processor 23, the light source device 24, the image processing device 25 and the image recording and reproduction apparatus 50, which are mounted on the second cart 12, the electric scalpel device 13, the insufflation device 14, the video processor 15 and the light source device 16, which are mounted on the first cart 11, and the surgical table 10 in a centralized manner. When communication is performed between the system controller 41 and the devices, the system controller 41 can display a setting screen of the setting states of the connected devices, operation switches and the like, on a display screen of the operation panel 49. The system controller 41 is configured to be capable of an operation and input, such as change of setting values, by a desired operation switch being touched to operate a predetermined area of the touch panel.

A remote control 30 is a second centralized operation device that an operating surgeon or the like residing in a sterilized area operates, and allows another device establishing communication to be operated through the system controller 41.

An infrared communication port (not shown) serving as communication means is attached to the system controller 41. The infrared communication port is provided at a position adjacent to the display device 19 or the like, which is easily irradiated with infrared light, and is connected to the system controller 41 through a cable.

The system controller 41 is connected to a patient monitor system 4 via a cable 9, and allows the patient monitor system 4 to analyze biological information, and cause a desired display device to display a result of the analysis.

Note that in the operating room 2, a camera 37 that picks up images of the medical devices, such as the surgical table 10, is provided. By picking up images of the medical devices, such as the surgical table 10, through the camera 37, and analyzing the picked up images, the operation states can be determined. A result of the determination, and the images picked up by the camera 37 are supplied to the system controller 41.

The video processors 15 and 23 are configured to be capable of generating endoscope images based on outputs from the respective endoscopes 31 and 32. The endoscope images from the video processors 15 and 23 are supplied to the image recording and reproduction apparatus 50. The video processors 15 and 23 and the image recording and reproduction apparatus 50 are connected to each other via a network, not shown, and various types of information including examination information are supplied from the video processors 15 and 23 to the image recording and reproduction apparatus 50 (not shown in FIG. 1). Note that communication lines of various communication standards can be adopted as the network that connects the video processors 15 and 23 and the image recording and reproduction apparatus 50 to each other.

In the present embodiment, it is configured to allow operation signals from various devices in the operating room 2 to be supplied to the image recording and reproduction apparatus 50 via a communication line of any of the various communication standards. For example, operation signals that include operation signals based on operations on various switches provided for the first endoscope 31 and the second endoscope 32, operation signals from medical devices, such as the electric scalpel device 13, operation signals of a foot switch, not shown, and operation signals of the operation panel 49 are supplied to the image recording and reproduction apparatus 50.

A head set type microphone 33 is allowed to be connected to the image recording and reproduction apparatus 50. The microphone 33 collects voices emitted by a wearer, and outputs a voice signal to the image recording and reproduction apparatus 50. Note that FIG. 1 only shows the single microphone 33, but multiple microphones 33 are connectable to the image recording and reproduction apparatus 50, and the image recording and reproduction apparatus 50 is configured to be capable of obtaining voices from the multiple microphones 33. Although the example where the microphone 33 is wiredly connected by a cable is shown, the microphone 33 may be one which can transmit a voice signal to the image recording and reproduction apparatus 50 through a wireless transmission path, such as of Wi-Fi (registered trademark) or Bluetooth (registered trademark).

In the operating room 2, a microphone 34 is provided while being supported by a supporting member, not shown. The microphone 34 is connected to the image recording and reproduction apparatus 50 via a cable, not shown, or a wireless transmission path, such as of a Wi-Fi or Bluetooth, and is configured to be capable of collecting voices in the operating room 2, and supplying voice signals to the image recording and reproduction apparatus 50.

FIG. 1 shows an example of a specific configuration of the image recording and reproduction apparatus 50 in FIG. 2.

The image recording and reproduction apparatus 50 is provided with a video input unit 52. The video input unit 52 is an interface suitable for image transmission, and captures various medical images (video signals). Note that the video input unit 52 can adopt any of various terminals, such as a DVI (digital visual interface) terminal, an SDI (serial digital interface) terminal, an RGB terminal, a Y/C terminal, and a video terminal. The video input unit 52 can obtain, for example, endoscope images from the video processors 15 and 23, and various medical images from an ultrasound device, an operative field camera, an X-ray observation device, an endoscope processor and the like that are different from the video processors 15 and 23.

Medical images captured by the video input unit 52 are supplied to a record data generation unit 55 that is a record data generation circuit. The record data generation unit 55 applies a predetermined encoding process to the inputted medical images, and thus converts the inputted medical images into video signals of a predetermined image format. For example, the record data generation unit 55 is configured to be capable of converting the inputted medical images into video signals of the MPEG2 format or MPEG-4AVC/H.264 format, and outputting the signals as record data.

In the present embodiment, the record data generation unit 55 is configured to be controlled by a record control unit 51 and to be capable of adding chapter information to the record data. For example, the record data generation unit 55 may be configured to include the chapter information, as meta information, in an image file that is record data, generate a file that is different from the image file and includes chapter information, or record the two types of chapter information.

The record control unit 51 is configured to be capable of control each unit of the image recording and reproduction apparatus 50 with respect to recording. The record control unit 51 may be what includes a processor, such as a CPU, not shown, and operate according to a program stored in a memory, not shown, to control each unit, or may include a field programmable gate array (FPGA) or the like.

In the present embodiment, the record control unit 51 is configured to classify the chapter information into chapter types, and set chapter information with respect to each chapter type, as described above. The record control unit 51 performs the setting of the chapter information with respect to each chapter type, on the basis of outputs of an operation and input unit 53 and an operation system determination unit 54.

The operation and input unit 53, which is an operation input device, is supplied with operation signals from various devices as operation instructors, via communication lines of various transmission standards. The operation and input unit 53 sometimes receives voice signals. The operation and input unit 53 includes, for example, multiple input ports that support a serial communication standard, such as RS232C, or a predetermined communication standard, and is, for example, configured to receive various operation signals that include operation signals based on operations on scope switches provided for the first endoscope 31 and the second endoscope 32 described above, operation signals from medical devices, such as the electric scalpel device 13, operation signals of a foot switch, not shown, and operation signals of the operation panel 49, via the corresponding input ports. The operation and input unit 53 is configured to output operation signals inputted via the corresponding input ports, to the operation system determination unit 54.

The image recording and reproduction apparatus 50 is provided with a display unit 62 that includes a display screen made up of an LCD (liquid crystal panel), or the like. The display unit 62, which is a display device, is configured to be capable of displaying medical images inputted via the video input unit 52, reproduction images of medical images stored in a storage unit 56, described later, on the display screen. The display unit 62 is configured to be capable of also displaying various menu screens related to control of the image recording and reproduction apparatus 50.

A touch panel 63 is provided on the display screen of the display unit 62. The touch panel 63 is configured to be capable of accepting a touch operation by a user onto the menu screen displayed on the display screen of the display unit 62, and outputting an operation signal based on the touch operation to the operation and input unit 53. The operation and input unit 53 is configured to also output the operation signal based on the user operation onto the touch panel 63 to the operation system determination unit 54. Note that the image recording and reproduction apparatus 50 may be provided an operation unit other than the touch panel 63, and a signal from the operation unit is also supplied to the operation system determination unit 54 via the operation and input unit 53.

The operation system determination unit 54, which is an operation system determination circuit, is configured to determine which device among devices including the touch panel 63 an operation signal inputted from the operation and input unit 53 is generated by an operation of the device (hereinafter, referred to as determination of the operation system), and output a determination result to the record control unit 51. For example, the operation system determination unit 54 may include an input port corresponding to the input port of the operation and input unit 53, and the operation and input unit 53 may supply the operation signal to the input port of the operation system determination unit 54 corresponding to the input port into which the operation signal is inputted. In this case, the operation system determination unit 54 may determine the operation system on the basis of which input port the operation signal is inputted to.

For example, the operation and input unit 53 may be configured to output, to the operation system determination unit 54, information on a number set on the input port into which the operation signal is inputted, instead of outputting the operation signal to the operation system determination unit 54. In this case, the operation system determination unit 54 may be configured to determine the device set on the input port of the operation and input unit 53 on the basis of the inputted information on the number, and output the determination result of the operation system to the record control unit 51.

If the operation signal includes ID information on the device having generated the operation signal, the operation system determination unit 54 may determine the operation system on the basis of the ID information, and output the determination result to the record control unit 51.

The record control unit 51 is supplied with the operation signal from the operation and input unit 53, and determines the chapter type about the operation signal, on the basis of the determination result supplied from the operation system determination unit 54. In other words, the record control unit 51 sets the same chapter type for operation signals about which the determination result indicating the same operation system is supplied, and sets a different chapter type for operation signals about which the determination result indicating a different operation system is supplied.

In other words, the record control unit 51 generates the chapter information on the chapter type corresponding to the operated device. The record control unit 51 is configured to use an embedded timer, not shown, to add time period information when the medical image is recorded by the record data generation unit 55. In other words, the record control unit 51 grasps a recording time (recording position) with reference to a recording start time of the record data generation unit 55, for example. Every time the determination result is received from the operation system determination unit 54, that is, every time the operation signal is inputted into the operation and input unit 53, the record control unit 51 generates the chapter information of the chapter type corresponding to the operation system, and outputs the information to the record data generation unit 55. The chapter information includes information on the operated device, and information on the recording time (recording position).

The record data generation unit 55 is configured to add the chapter information of each chapter type from the record control unit 51, as metadata (hereinafter, chapter information metadata), to the medical image from the video input unit 52, or create a table (hereinafter, referred to as a chapter information table) including the chapter information of each chapter type, beside the medical image from the video input unit 52. The record data generation unit 55 is configured to adopt the medical image and the chapter information table as record data, or adopt the medical image including the chapter information metadata as record data, and output the generated record data to the storage unit 56. For example, a hard disk device or a memory medium may be adopted as the storage unit 56. The storage unit 56 is controlled by the record control unit 51 to record the record data as an image file.

In an operation, an examination and the like, persons who operate the medical devices are often predetermined. For example, persons who operate the scope switches of the endoscopes 31 and 32, a person who operates the foot switch, and a person who operates the touch panel 63 are often different from each other and predetermined. In such a case, determination of the operation system for determining the device where the operation signal occurs is conceivable as determination by a person. Consequently, in this case, it can be said that the record control unit 51 sets the chapter types different among persons and generates the chapter information.

FIGS. 3 and 4 are explanatory diagrams for illustrating the chapter information, FIG. 3 shows an example of the chapter information table, and FIG. 4 shows an example of the chapter information metadata.

In FIG. 3, System1, System2, and System3 indicate chapter types, and correspond to devices as operation instruction units, or persons. The example in FIG. 3 shows the chapter information about three chapter types corresponding to respective three devices (or persons). Every time the operation signal is inputted, the record control unit 51 writes, for example, time period information from the start of recording, as information on the chapter position, in the field of the corresponding chapter type. In FIG. 3, for example, as for the chapter type designated by System2, it is shown that the chapter information is set at the positions of 7 minutes and 40 seconds, 22 minutes and 12 seconds, and 30 minutes and 15 seconds from the start of recording.

FIG. 4 shows an example of chapter information metadata that includes the same chapter information as the chapter information table in FIG. 3. FIG. 4 indicates the three chapter types that are System1, System2, and System3 in FIG. 3 by [Sys1ChapterInfo], [Sys2ChapterInfo], and [Sys3ChapterInfo], respectively. Every time the operation signal is inputted, the record control unit 51 writes, for example, time period information from the start of recording, as information on the chapter position, in the field of the corresponding chapter type. In FIG. 4, for example, as for the chapter type designated by [Sys2ChapterInfo], it is shown that the chapter information is set at a position of 7 minutes and 40 seconds from the start of recording, by Sys02chap001=00:07:40 indicating the first chapter information. Likewise, it is shown that the chapter information is set at positions of 22 minutes and 12 seconds and 30 minutes and 15 seconds by Sys02chap002=00:22:12 and Sys02chap003=00:30:15, respectively.

The image recording and reproduction apparatus 50 is provided with a reproduction control unit 61. The reproduction control unit 61 is configured to be capable of controlling each unit of the image recording and reproduction apparatus 50 with respect to reproduction. The reproduction control unit 61 may be what includes a processor, such as a CPU, not shown, and operate according to a program stored in a memory, not shown, to control each unit, or may include a field programmable gate array (FPGA) or the like.

The reproduction control unit 61 can read the record data from the storage unit 56, and output the record data to the display unit 62 or a video output unit 64. The reproduction control unit 61 is configured to be capable of designating the chapter type (chapter system) designated on the basis of the operation signal from the operation and input unit 53 during record data reading. When the chapter type is designated by the reproduction control unit 61, the storage unit 56 allows only information on the designated chapter type to be outputted. Alternatively, when reading the record data from the storage unit 56, the reproduction control unit 61 may add information for enabling only the designated chapter type to the data, and output the information.

The video output unit 64 is configured to be supplied with the inputted record data, that is, the medical image including the chapter information, and display the medical image including the menu indication for designating the chapter, on the display screen of an external monitor 66. Likewise, the display unit 62 is configured to be supplied with the medical image including the chapter information, and display the medical image including the menu indication for designating the chapter, on the display screen. During reproduction, the operation signal from the touch panel 63 for the menu indication is supplied to the reproduction control unit 61 through the operation and input unit 53. In response to the operation of the touch panel 63, the reproduction control unit 61 can perform movement of a reproduction position, selection of the chapter type and the like. For example, when the movement of the reproduction position by the chapter is designated, the reproduction control unit 61 controls the storage unit 56 to reproduce the medical image at the reproduction position. When an operation of selecting the chapter type is performed, the reproduction control unit 61 controls the storage unit 56 to output the chapter information of the selected chapter type.

Figures 5, 6:
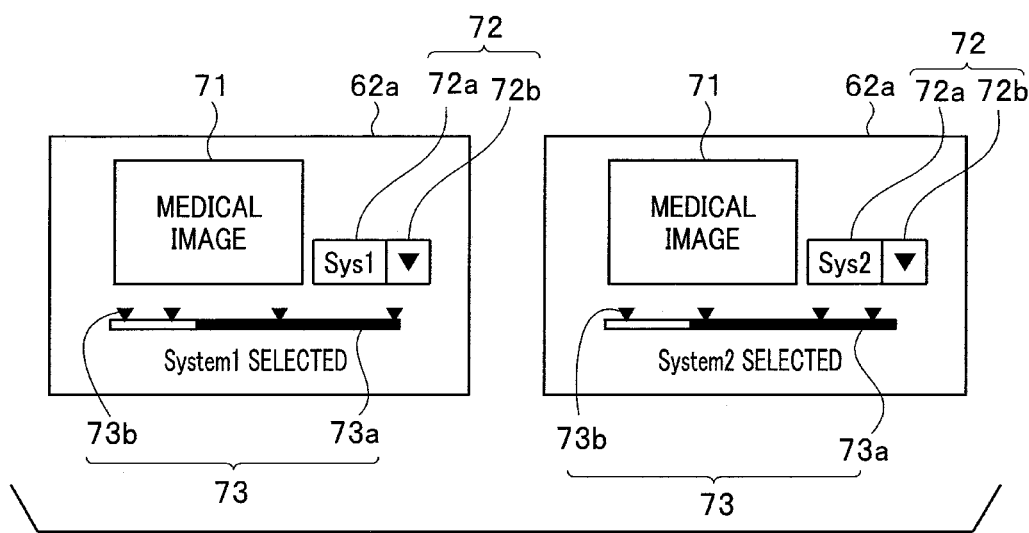
FIG. 5 is an explanatory diagram showing display examples of medical images and menu indications displayed on a display screen 62a of a display unit 62.
FIG. 6 is an explanatory diagram showing an example of chapter information added to a medical image and outputted.

FIG. 5 is an explanatory diagram showing display examples of medical images and menu indications displayed on a display screen 62a of the display unit 62. The display examples of the display screen 62a shown to the left and right of FIG. 5 indicate displays of the same medical image at the same reproduction position.

As shown in FIG. 5, on the display screen 62a, a display area 71 is provided, and a type selection indication 72 for selecting the chapter type, and a time bar indication 73 that indicates a current reproduction position and a chapter position are displayed. In the display area 71, a medical image is displayed. In the type selection indication 72, a selection indication 72a that indicates a selected chapter type in a pull-down menu, and a mark 72b for displaying a pull-down menu for selecting the chapter type, are displayed.

For example, by the user applying a touch operation onto the mark 72b, the reproduction control unit 61 can control display of the display unit 62 to display the pull-down menu for selecting the chapter type. By the user applying a touch operation of selecting the chapter type from the displayed pull-down menu, the reproduction control unit 61 controls the storage unit 56 to select and output the chapter information of the selected chapter type. The reproduction control unit 61 controls display of the display unit 62 to display the selection indication 72a that indicates the selected chapter type. The left side of FIG. 5 shows that an indication of Sys1 shows that System1 in FIG. 3 or the chapter type of [Sys1ChapterInfo] in FIG. 4 is selected, and the right of FIG. 5 shows that an indication of Sys2 shows that System2 in FIG. 3 or the chapter type of [Sys2ChapterInfo] in FIG. 4 is selected.

The time bar indication 73 on the display screen 62a includes: a reproduction position indication 73a indicating that the boundary position between a non-hatching portion and a filled portion of the medical image displayed in the display area 71 is a current reproduction position; and a chapter position indication 73b indicating the positions of chapters added to the medical image. Even with reproduction of the same medical image, the chapter types of System1 and System2 have chapter information adding positions different from each other. In the example in FIG. 5, for the chapter type of System1, the current reproduction position exceeds the second chapter position, while for the chapter type of System2, the current reproduction position is before the second chapter position.

As shown in FIG. 5, the time bar indication 73 corresponding to the chapter type designated by the user's selection can be displayed, and control of the reproduction position based on the chapter information of the designated chapter type can be achieved. The user can add the chapter information of the chapter type corresponding to the device that the user himself operates, to the medical image, and record the medical image, and, by designating and displaying the chapter information, cue reproduction at the chapter position designated by the user himself operating the device can be easily performed.

Note that in the aforementioned description, the example is described where, by performing a touch operation on the type selection indication 72 using the touch panel 63, the chapter information can be switched; the reproduction control unit 61 may switch the chapter information on the basis of the operation signal from the device. For example, when the scope switches of the endoscopes 31 and 32 are operated during reproduction, the reproduction control unit 61 receives the operation signal based on the operation from the operation and input unit 53, and controls the storage unit 56 so as to selectively read the chapter information of the chapter type corresponding to the operation. Accordingly, through use of the device having performed the operation of designating the chapter during recording, cue reproduction using the chapter information of the chapter type based on the operation of the device during reproduction can be allowed.

The reproduction control unit 61 can read the record data from the storage unit 56, supply the record data to the record data generation unit 55, cause the record data generation unit 55 to newly generate chapter information to be added to the medical image, and subsequently output the chapter information to an external medium writing unit 65. In this case, the reproduction control unit 61 is configured to be capable of designating the chapter type (chapter system) on the basis of the operation signal from the operation and input unit 53. In other words, when the chapter type is designated during output of the record data to an external device, the reproduction control unit 61 allows only information on the chapter type designated from the storage unit 56 to be outputted. For example, the user can designate the chapter type of the chapter information to be added during output of the medical image to the external device, by an operation onto the touch panel 63. Note that the user can designate one or more chapter types, and the record data generation unit 55 is controlled by the reproduction control unit 61 to be capable of outputting the medical image to which the chapter information of all the designated chapter types is added.

FIG. 6 is an explanatory diagram showing an example of the chapter information added to the medical image and outputted. The example in FIG. 6 shows an example in a case where the chapter type of [Sys1ChapterInfo] in FIG. 4 is selected. In FIG. 6, the chapter information Sys01chap001=00:05:25, Sys01chap002=00:19:36 and Sys01chap003=00:30:03 in FIG. 4 are described in [ChapterInfo].

The external medium writing unit 65 is configured to allow the record data from the storage unit 56 to be supplied to an external medium 67 that is an external recording medium, not shown, and recorded. Note that not only a BD (Blue-ray Disk), DVD, and USB but also a server or the like on a network may be adopted as the external medium 67, or another recording medium may be adopted.

Figure 7:
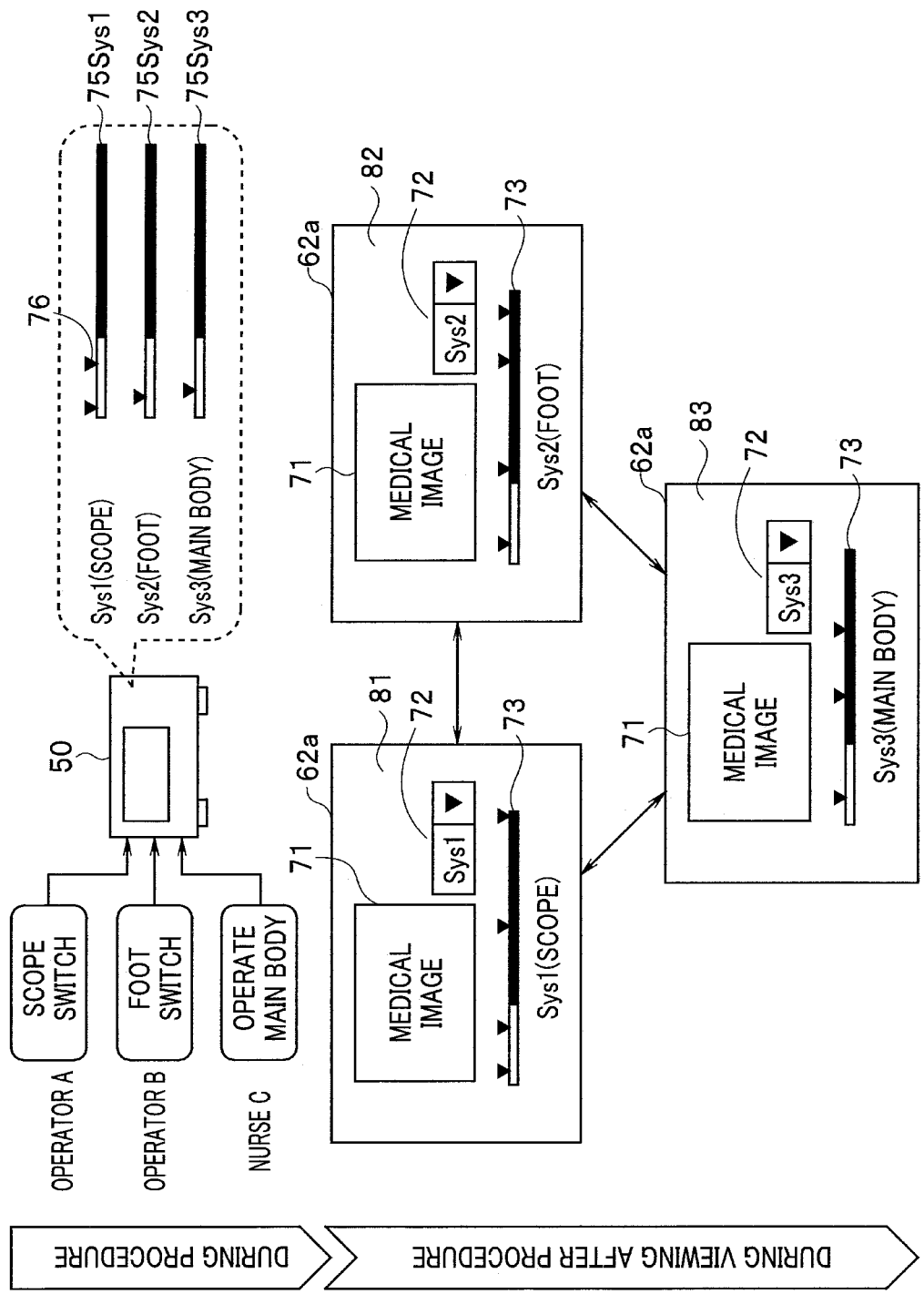
FIG. 7 is an explanatory diagram for illustrating an operation of a first embodiment.

Next, the operation of the embodiment having such a configuration is described with reference to FIG. 7. FIG. 7 is an explanatory diagram for illustrating the operation of the first embodiment.

FIG. 7 shows the vertical axis indicating the time during the procedure, after the procedure, and during viewing, and is for illustrating the operation during the procedure, and the operation after the procedure and during viewing. During the procedure, the image recording and reproduction apparatus 50 records the medical image inputted via the video input unit 52. The record data generation unit 55 is controlled by the record control unit 51 to generate the record data on the medical image, which is then supplied to the storage unit 56 and stored.

The scope switch is operated by an operator A, the foot switch is operated by an operator B, the touch panel 63 (main body operation) of the image recording and reproduction apparatus 50 is operated by a nurse C. Operation signals based on these operations are supplied to the operation and input unit 53 of the image recording and reproduction apparatus 50.

The operation system determination unit 54 determines the operation system of each operation inputted into the operation and input unit 53, and outputs a determination result to the record control unit 51. The record control unit 51 generates the chapter information on the chapter type corresponding to each operation system, which is then supplied to the record data generation unit 55. Accordingly, the record data generation unit 55 records the chapter information corresponding to the recording time of the medical image inputted from the video input unit 52, together with the chapter type information. Note that as described above, the chapter information is recorded as the chapter information table or the chapter information metadata. Accordingly, the operator A, the operator B, and the nurse C can add chapters to the medical image to be recorded, at timing that each person intends.

FIG. 7 shows situations of recording the chapter information by time bars 75Sys1, 75Sys2 and 75Sys3. Note that in FIG. 7, positions (time points) to which chapter information is added by the operation of the scope switch by the operator A are indicated by chapter position indications 76 on the time bar 75Sys1 indicated by Sys1 (scope), positions (time points) to which chapter information is added by the operation of the foot switch by the operator B are indicated by chapter position indications 76 on the time bar 75Sys2 indicated by Sys2 (foot), and positions (time points) to which chapter information is added by the main body operation by the nurse C are indicated by chapter position indications 76 on the time bar 75Sys3 indicated by Sys3 (main body).

Note that three medical images are not necessarily recorded by the record data generation unit 55, but the chapter information including information on three chapter types is added to one medical image instead. The example in FIG. 7 shows that at a stage where recording is performed to the boundary positions between the non-hatching portions and the filled portions of the time bars 75Sys1, 75Sys2 and 75Sys3, chapters are added to time points indicated by two chapter position indications 76 by the operation of the scope switch by the operator A, a chapter is added to a time indicated by one chapter position indication 76 by the operation of the foot switch by the operator B, and a chapter is added to a time indicated by one chapter position indication 76 by the main body operation by the nurse C.

After the procedure is finished, for example, based on a user operation, the record control unit 51 instructs the record data generation unit 55 to finish recording. Accordingly, the medical image including the chapter information as metadata, or the medical image with which the chapter information is associated as a table is filed and recorded in the storage unit 56.

Next, after the procedure or during viewing, reproduction is performed. Note that in FIG. 7, a state after the procedure is, for example, a state where each unit in FIG. 2 is left connected electrically, and a state where operation signals from the endoscopes 31 and 32 can be supplied to the operation and input unit 53 is shown. In this case, a reproduction instruction, such as for a cue to a chapter position, may be issued not only through the touch panel 63 but also through an operation of any of the devices. A state during viewing is a state where electric connection of each unit in FIG. 2 is canceled, and a reproduction instruction, such as for a cue to a chapter position, is performed through the touch panel 63.

For example, when reproduction is instructed by an operation of the touch panel 63, the reproduction control unit 61 displays a reproduction image 81, 82 or 83 in FIG. 7 on the display screen 62a of the display unit 62. The shown reproduction images 81 to 83 are similar to the images in FIG. 5, and the type selection indication 72 for selecting the chapter type and the time bar indication 73 are included out of the display area 71 for the medical image. The reproduction image 81 is an image corresponding to the indication of the chapter type based on the operation of the scope switch by the operator A, the reproduction image 82 is an image corresponding to the indication of the chapter type based on the operation of the foot switch by the operator B, the reproduction image 83 is an image corresponding to the indication of the chapter type based on the main body operation by the nurse C.

By selecting Sys1 (scope) through the type selection indication 72, the operator A can perform cue reproduction using the chapter information added by the scope switch operation by himself. Likewise, by selecting Sys2 (foot) through the type selection indication 72, the operator B can perform cue reproduction using the chapter information added by the foot switch operation by himself. By selecting Sys3 (main body) through the type selection indication 72, the nurse C can perform cue reproduction using the chapter information added by the main body operation by himself.

Note that the example has been described where the reproduction control unit 61 displays the recorded medical image on the display unit 62, but display may be made on the external monitor 66 instead. In this case, the reproduction control unit 61 reads the medical image to which the chapter information is added, from the storage unit 56, and outputs the medical image to the video output unit 64. The video output unit 64 supplies the inputted medical image to the external monitor 66, and achieves display similar to the display of the images 81 to 83 in FIG. 7. Also in this case, by the operation of an operation portion, not shown, of the external monitor 66 or the operation of the touch panel 63, reproduction control, such as chapter type switching and cuing, can be performed.

Next, for example, it is assumed that through the touch panel 63, an instruction of writing of the medical image to the external device is issued. A typical reproduction apparatus cannot perform cuing control with multiple chapter types being recognized. In this case, the chapter information of the chapter type that the user intends is selectively added to the medical image. When a writing request that includes designation of the chapter type and is for the external device is generated from the operation and input unit 53, the reproduction control unit 61 performs control for selectively adding the chapter information of the designated chapter type to the medical image.

In other words, the storage unit 56 is controlled by the reproduction control unit 61 to output the recorded medical image to the record data generation unit 55 and selectively output only the chapter information of the designated chapter type to the record data generation unit 55. The record data generation unit 55 adds the chapter information of the designated chapter type to the medical image, and outputs the medical image to the external medium writing unit 65. The external medium writing unit 65 supplies the external medium 67 with the medical image to which the chapter information is added, and thus records the medical image.

Even when the medical image recorded in the external medium 67 is reproduced by a typical reproduction apparatus, cue reproduction to the chapter position based on the chapter information of the designated chapter type is allowed. Note that the reproduction control unit 61 can perform control so as to select chapter information of a plurality of chapter types, which is added to the medical image.

As described above, in the present embodiment, based on the operation signal from each device, chapter information of the chapter type of the corresponding device is generated and added to the medical image. Accordingly, in a case where a person who operates each device is predetermined, the chapter information of the chapter type on a device-by-device basis, that is, a person-by-person basis can be recorded, and during reproduction, cue reproduction at the chapter position corresponding to the operation on a person-by-person basis (device-by-device basis) is allowed. Thus, each user can perform cue reproduction using the chapter set at timing that user himself intends, and significantly improve convenience during viewing and editing.

Second Embodiment

FIGS. 8 to 11 are explanatory diagrams for illustrating a second embodiment of the present invention. The hardware configuration of the present embodiment is similar to the hardware configuration of FIG. 1.

In the first embodiment, it is assumed that the person operating the device during an operation or the like is fixed, and the chapter information of the chapter type corresponding to the device is recorded, which allows cue reproduction at the chapter position set by each user himself. Unlike the first embodiment, the present embodiment allows cuing at the chapter position set by each user himself even in a case where devices and persons operating the devices do not have one-to-one correspondence.

In the present embodiment, information for identifying the persons operating the respective devices is added to operation signals inputted from the devices into the operation and input unit 53. For example, in a case of operating the touch panel 63, each user may input ID information identifying himself and subsequently perform an operation for setting the chapter. It may be configured that information identifying each user is added to the operation signal from the touch panel 63, by displaying a GUI (graphical user interface) indication for each user on the display unit 62. In the operations of the scope switches of the endoscopes 31 and 32, multiple times of turning on and off the scope switches may be performed to obtain the information identifying the operator, through the number of times.

The operation system determination unit 54 is configured to determine the device issuing the inputted operation signal by a method similar to the method of the first embodiment, from the output of the operation and input unit 53 and, at the same time, determine the operator and output a determination result to the record control unit 51. The record control unit 51 classifies the chapter information into chapter types on a device-by-device basis and a person-by-person basis, issues the chapter information of the chapter type based on the determination result, and outputs the chapter information to the record data generation unit 55. In other words, the chapter information includes information on the operated device and the operator, and information on the recording time (recording position).

The record data generation unit 55 is configured to add the chapter information on each chapter type from the record control unit 51, as chapter information metadata, to the medical image from the video input unit 52, or create a chapter information table including the chapter information on each chapter type, beside the medical image from the video input unit 52. The record data generation unit 55 is configured to adopt the medical image and the chapter information table as record data, or adopt the medical image including the chapter information metadata as record data, and output the generated record data to the storage unit 56. The storage unit 56 is controlled by the record control unit 51, and records, as an image file, the record data on the medical image to which the chapter information is added.

FIG. 8 shows an example of the chapter information table in the second embodiment, and FIG. 9 shows an example of the chapter information metadata in the second embodiment.

In FIG. 8, System1, System2, and System3 indicate discrimination among devices, and users indicate discrimination among persons operating the respective devices. The example in FIG. 8 shows the chapter information about chapter types corresponding to three devices and three users. Every time the operation signal is inputted, the record control unit 51 writes, for example, time period information from the start of recording, as information on the chapter position, in the field of the chapter type assigned with respect to each person operating the corresponding device. In FIG. 8, for example, as for the chapter type of the user A operating the device designated by System2, it is shown that the chapter information is set at the positions of 7 minutes and 40 seconds, and 22 minutes and 12 seconds from the start of recording. Note that as for the chapter type corresponding to the user C operating the device designated by System2, it is shown that the chapter information is set at the position of 30 minutes and 15 seconds from the start of recording.

FIG. 9 shows an example of chapter information metadata that includes the same chapter information as the chapter information table in FIG. 8. FIG. 9 indicates the three devices that are System1, System2, and System3 in FIG. 8 by [Sys1ChapterInfo], [Sys2ChapterInfo], and [Sys3ChapterInfo], respectively. Every time the operation signal is inputted, the record control unit 51 writes, for example, time period information from the start of recording, as information on the chapter position, in the field of the chapter type assigned with respect to each person operating the corresponding device. In FIG. 9, for example, as for the chapter type designated by [Sys2ChapterInfo], it is shown that the chapter information is set by the user A operating the device of System2 at timing of 7 minutes and 40 seconds from the start of recording, by Sys02_USER_Achap001=00:07:40 indicating the first chapter information. Likewise, it is shown that the chapter information is set by the user C operating the device of System2 at the position of 30 minutes and 15 seconds from the start of recording, by Sys02_USER_Cchap003=00:30:15.

The reproduction control unit 61 can perform cue reproduction using the chapter information on a user-by-user basis and a device-by-device basis, by utilizing the chapter information table or the chapter information metadata. For example, the reproduction control unit 61 can perform cue reproduction at the chapter positions by all the devices operated by the user A, and also perform cue reproduction at the chapter positions based on the operation signals from the device of System1 operated by all the users. The reproduction control unit 61 can perform cue reproduction according to the chapter information by a predetermined device operated by a predetermined user.

Figures 10, 11:
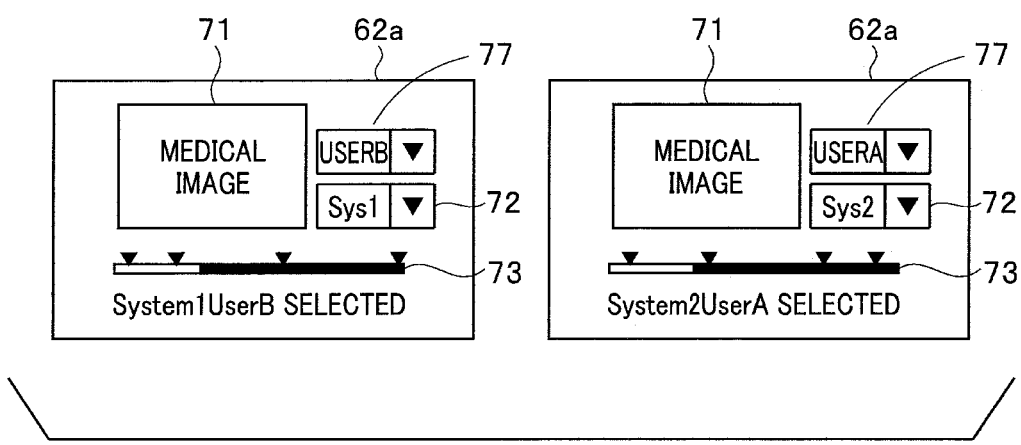
FIG. 10 is an explanatory diagram for illustrating the second embodiment of the present invention.
FIG. 11 is an explanatory diagram for illustrating the second embodiment of the present invention.

FIG. 10 shows a display corresponding to FIG. 5, shows an example of an image display during reproduction, and shows, for example, a display example of a medical image and a menu indication that are displayed on the display screen 62a of the display unit 62. In FIG. 10, indications identical to the indications in FIG. 5 are assigned the same symbols, and the description is omitted. The display examples of the display screen 62a shown to the left and right of FIG. 10 indicate displays of the same medical image at the same reproduction position.

As shown in FIG. 10, in the present embodiment, a user selecting display 77 is provided. The type selection indication 72 displayed on the display screen 62a is for selecting the device, and is configured to allow any or all of System1 to System3 to be designated. The user selecting display 77 is for selecting the user, and is configured to allow any or all of the users A to user C to be designated.

The left side of FIG. 10 shows a display for using the chapter information set by the user B operating the device indicated by System1, and the right side of FIG. 10 shows a display for using the chapter information set by the user A operating the device indicated by System2. Through selection operations using the type selection indication 72 and the user selecting display 77, for example, reproduction using the entire chapter information set by operating the device indicated by System1 can be achieved, and for example, reproduction using the entire chapter information set on the basis of operation signals from all the devices operated by the user A can be achieved.

The reproduction control unit 61 can control the storage unit 56 and the record data generation unit 55 to supply the external medium writing unit 65 with the medical image to which any chapter type is added, and causes the external medium writing unit 65 to output the medical image to the external device.

FIG. 11 is an explanatory diagram showing an example of the chapter information added to the medical image and outputted. The example in FIG. 11 shows an example in a case where the chapter type of all the users of [Sys1ChapterInfo] in FIG. 9 is selected. Also during writing to the external device, the reproduction control unit 61 can designate any chapter type on a user-by-user basis, a device-by-device basis, with respect to each user and device or the like.

The other components and operations are similar to the components and operations of the first embodiment.

As described above, the present embodiment can obtain advantageous effects similar to the effects of the first embodiment. Furthermore, in the present embodiment, even in a case where the users and the devices operated by the users do not have one-to-one correspondence, the chapter types on a user-by-user basis, a device-by-device basis, or with respect to each user and device can be set, and the chapter information can be added to medical images. Accordingly, the user can perform cue reproduction at the chapter position and the like set and intended by himself.

Third Embodiment

Figure 12:
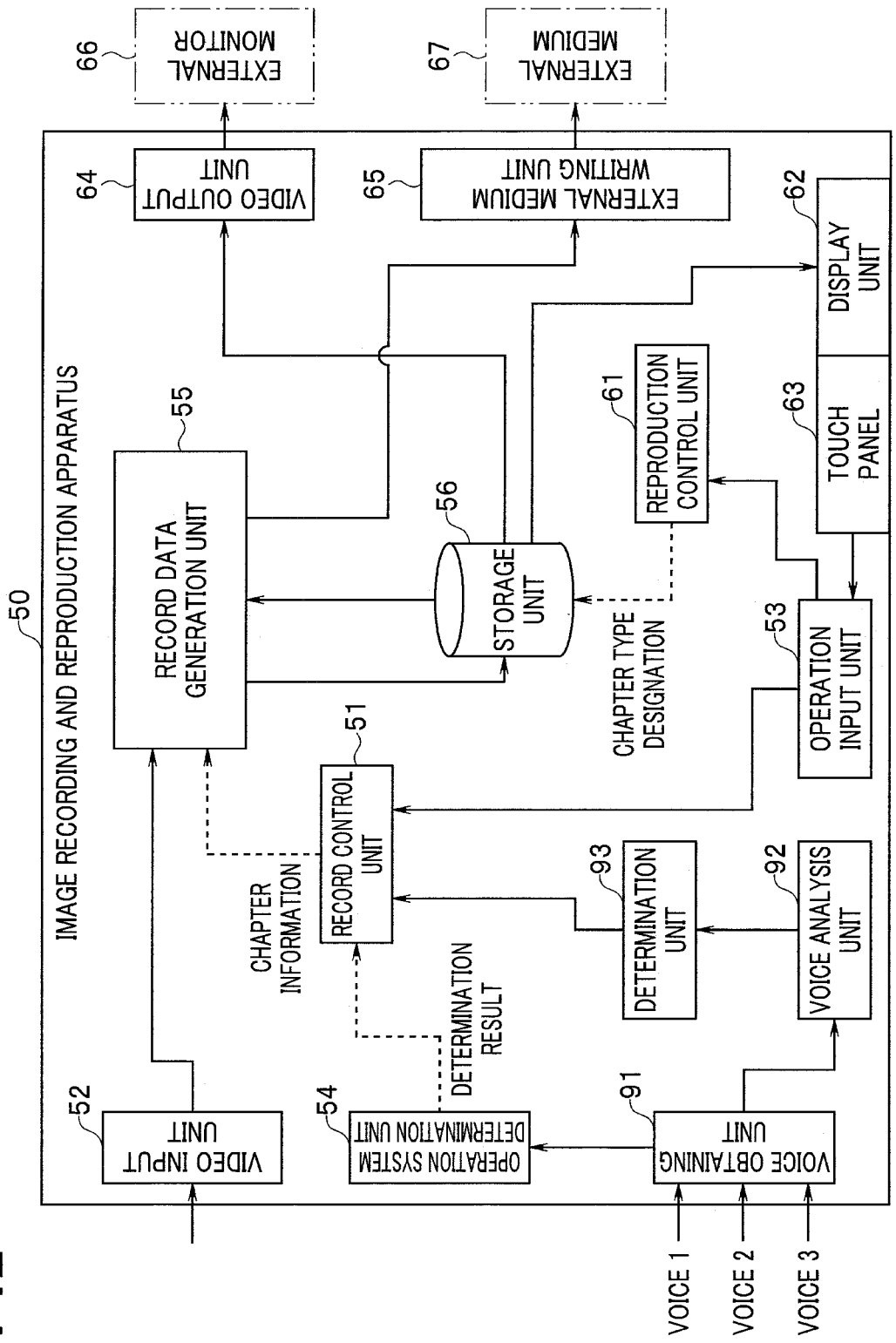
FIG. 12 is a block diagram showing a third embodiment of the present invention.

FIG. 12 is a block diagram showing a third embodiment of the present invention. In FIG. 12, configuration elements identical to the configuration elements in FIG. 1 are assigned the same symbols, and the description is omitted. The present embodiment allows the chapter information to be added by voice input.

In the present embodiment, the image recording and reproduction apparatus 50 is provided with a voice obtaining unit 91. Voice signals (a voice 1, a voice 2, and a voice 3) from the microphones 33 and 34 and the like are inputted into the voice obtaining unit 91, which is a voice input device. The voice obtaining unit 91 is made up of connectors and the like to which cables are connected in a case where the transmission path for an inputted voice signal is wired, while being made up of an antenna, a receiver and the like receiving a wireless signal in a case where the transmission path for an inputted voice signal is wireless, and captures the inputted voice signal and outputs the voice signal to a voice analysis unit 92.

The voice signal obtained by the voice obtaining unit 91 is supplied to the operation system determination unit 54. The operation system determination unit 54 can detect which microphone each voice signal has been collected from. For example, the operation system determination unit 54 can detect which microphone has collected the voice signal by means of the connectors connected to the respective cables in the case where the voice signal is wiredly transmitted, and can detect which microphone has collected the voice signal by means of a device ID obtained at establishment of wireless communication, for example, in the case where the voice signal is wirelessly transmitted.

The voice analysis unit 92 applies an analysis process to the inputted voice, and obtains a voice analysis result. For example, the voice analysis unit 92 performs voice recognition using a voice model, a word dictionary, and a language model which are preliminarily prepared for the system. For example, the voice analysis unit 92 analyzes speech content of doctors and nurses collected through the microphones 33 and 34 by a voice recognition process, obtains a voice recognition result of words and conversations made by the doctors and nurses, and outputs the result as an analysis result to a determination unit 93. The determination unit 93 is configured to determine whose voice the collected voice by the microphone 33, 34 or the like is, and output a judgement result to the record control unit 51.

Thus, the record control unit 51 is supplied with the judgement result of the microphone used for sound collection, from the operation system determination unit 54, and with the judgement result of the person having spoken, from the determination unit 93. Every time the determination result of a voice of a person is obtained from the determination unit 93, the record control unit 51 generates and outputs the chapter information of the chapter type with respect to each microphone (device) and each person.

The other components and operations are similar to the components and operations of the second embodiment.

As described above, in the present embodiment, by determining a voice of a person and the microphone used to collect the voice, the chapter information of the chapter type on a device-by-device basis and a person-by-person basis can be added to the medical image, and advantageous effects similar to the advantageous effects of the second embodiment can be obtained. The present embodiment has an advantage that the chapter information can be set by a voice, and the operator and the like can concentrate on procedures themselves.

The present invention is not limited as it is to each of the embodiments, and the configuration elements can be modified and embodied in a range without departing from the gist in an implementation stage. By appropriately combining the multiple configuration elements disclosed in each of the embodiments described above, various inventions can be formed. For example, some configuration elements among all the configuration elements described in the embodiments may be removed. Configuration elements in the different embodiments may be appropriately combined.

For example, in the embodiments, parts described as units (or sections) may be configured by dedicated circuits or by combining multiple general circuits, or may be configured by combining processors, such as microprocessors and CPUs, performing operations according to preliminarily programmed software, or sequencers, as required.

What is claimed is:

1. An image recording and reproduction apparatus comprising:
    a processor comprising hardware, wherein the processor is configured to:
        generate record data based on an inputted video signal;
        determine an operation signal of an operation by operators, the operation signal being from each of a plurality of medical devices;
        determine the operators performing the operation of each of the medical devices;
        generate a chapter categorized for each of the medical devices and the operators;
        assign metadata about the operation signal and the operators to the video signal;
        classify the chapter based on the metadata; and
        assign the metadata about the operation signal, the operators and the time period information from a start of recording the record data.
2. The image recording and reproduction apparatus according to claim 1,
    wherein the processor is configured to record the metadata on the record data.
3. The image recording and reproduction apparatus according to claim 1,
    wherein the processor is configured to determine the operators performing the operation of each of the medical devices, based on which input port the operation signal is inputted into among a plurality of input ports.
4. The image recording and reproduction apparatus according to claim 1,
    wherein the processor is configured to determine the operators performing the operation of each of the medical devices, based on information included in the operation signal.
5. The image recording and reproduction apparatus according to claim 1,
    wherein the processor is configured to:
        associate and record the record data with the chapter generated; and
        control reproduction of the record data with which the chapter is associated and recorded, and use only the chapter of a category of a designated medical device and a designated operator, from among the medical devices and operators, designated by a user for reproduction control.
6. The image recording and reproduction apparatus according to claim 5,
    wherein the processor is configured to cause a display to display a selection indication for selecting the category of the designated medical device and the designated operator to be used for the reproduction control.
7. The image recording and reproduction apparatus according to claim 6,
    wherein the processor is configured to cause the display to display a time bar indication indicating a recording position of the chapter of the category of the designated medical device and the designated operator, with an image based on the record data.
8. The image recording and reproduction apparatus according to claim 5,
    wherein the processor is configured to:
        add the chapter to the record data and record the record data during a procedure; and
        after completion of the procedure, select the category of the designated medical device and the designated operator; and
        use the category of the designated medical device and the designated operator for the reproduction control.
9. The image recording and reproduction apparatus according to claim 1,
    wherein the processor is configured to:
        associate and record the record data with the chapter generated; and
        control reproduction of the record data with which the chapter is associated and recorded, and output the record data that only enables the chapter of the category of a designated medical device and a designated operator, from among the medical devices and operators, designated by a user.
10. The image recording and reproduction apparatus according to claim 1,
    wherein the processor is configured to:
        receive a plurality of pieces of voice information; and
        determine the operators performing the operation of each of the medical devices, based on the voice information received.

11. An endoscope system comprising:
   the image recording and reproduction apparatus according to claim 1; and
   an endoscope,
   wherein the endoscope is one of the plurality of medical devices.

12. An image recording method comprising:
   generating record data based on an inputted video signal;
   determining an operation signal of an operation by operators, the operation signal being from each of a plurality of medical devices;
   determining the operators performing the operation of each of the medical devices;
   generating a chapter categorized for each of the medical devices and the operators;
   assigning metadata about the operation signal and the operators to the video signal;
   classifying the chapter based on the metadata; and
   assigning the metadata about the operation signal, the operators and the time period information from a start of recording the record data.

* * * * *